United States Patent [19]

Harris et al.

[11] 4,182,877
[45] Jan. 8, 1980

[54] SUBSTITUTED ANTHRANILATES

[75] Inventors: Roger L. N. Harris, Aranda; John L. Huppatz, Weetangera; John N. Phillips, Yarralumla; Barbara Witrzens, Holt, all of Australia

[73] Assignee: Commonwealth Scientific and Industrial Research Organization, Campbell, Australia

[21] Appl. No.: 795,595

[22] Filed: May 10, 1977

[30] Foreign Application Priority Data

May 12, 1976 [AU] Australia ............................. PC5901

[51] Int. Cl.$^2$ .................. C07D 295/06; A61K 31/245
[52] U.S. Cl. .................................... 544/172; 546/237;
260/326.8; 260/454; 260/574; 424/310;
424/330; 424/248.55; 424/267; 424/274;
560/47
[58] Field of Search .......... 560/47; 260/247.2, 518 A,
260/326.8; 544/172; 546/237

[56] References Cited
PUBLICATIONS

Harris et al., Angew Chem. Int. Ed. Engl., vol. 15(8) 1976.
Michaelis et al., Ber. Dtsch. Chem. Ges., 34, 2284 (1901).

*Primary Examiner*—James O. Thomas, Jr.
*Assistant Examiner*—G. T. Breitenstein
*Attorney, Agent, or Firm*—Sughrue, Rothwell, Mion, Zinn and Macpeak

[57] ABSTRACT

Anthranilic acid derivatives exhibiting fungicidal properties and useful as synthesis intermediates have the formula:

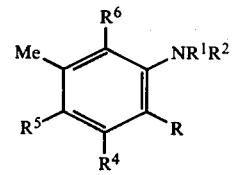

wherein
R is selected from the group consisting of a hydrogen atom; a —COOR$^3$ group and a —CH$_2$OH group; R$^1$ and R$^2$ are the same or different and selected from the group consisting of a hydrogen atom and alkyl and cycloalkyl groups (provided that R$^1$ and R$^2$ are not both hydrogen atoms), or R$^1$ and R$^2$, together with the nitrogen atom to which they are attached, form a non-aromatic heterocyclic ring structure;
R$^3$ is selected from the group consisting of a hydrogen atom and an alkyl group;
R$^4$ is selected from the group consisting of a hydrogen atom, a halogen atom and a hydroxyl group;
R$^6$ is selected from the group consisting of a hydrogen atom and a halogen atom; and
R$^5$ is selected from the group consisting of a hydrogen atom, a halogen atom, and nitro, thiocyano and formyl groups.

A process for production of these compounds by self-condensation of a substituted aminocrotonate by phosphorous oxychloride is also disclosed.

6 Claims, No Drawings

SUBSTITUTED ANTHRANILATES

This invention concerns anthranilic acid derivatives which exhibit fungicidal properties, and to a process for the production thereof.

According to the present invention, there is provided a compound of the formula I:

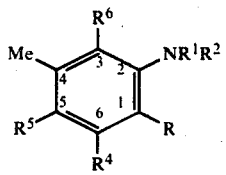

wherein
R is selected from the group consisting of a hydrogen atom, a —COOR$^3$ group and a —CH$_2$OH group;
R$^1$ and R$^2$ are the same or different and selected from the group consisting of a hydrogen atom, and alkyl (preferably containing from 1 to 6 carbon atoms) and cycloalkyl (preferably containing from 5 to 10 carbon atoms) groups (provided that R$^1$ and R$^2$ are not both hydrogen atoms), or R$^1$ and R$^2$, together with the nitrogen atom to which they are attached, form a non-aromatic heterocyclic ring structure (preferably a 5- or 6- membered heterocyclic ring structure such as a pyrrolidino, piperidino or morpholino group);
R$^3$ is selected from the group consisting of a hydrogen atom and an alkyl (preferably containing from 1 to 6 carbon atoms) group;
R$^4$ is selected from the group consisting of a halogen atom and a hydroxyl group;
R$^6$ is selected from the group consisting of a hydrogen atom and a halogen atom; and
R$^5$ is selected from the group consisting of a hydrogen atom, a halogen atom, and nitro, thiocyano and formyl groups.

Preferably, the compound is a compound of the formula II

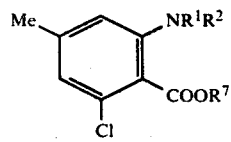

wherein R$^1$ and R$^2$ are as defined above, and R$^7$ is an alkyl (preferably containing from 1 to 6 carbon atoms) group.

Compounds of the formula I have shown activity against the fungus, *Tilletia foetida* (the organism responsible for bunt or wheat smut), and in the control of *Verticillium dahliae* on tomato plants. In addition, these compounds are valuable intermediates which can be transformed into a variety of derivatives related to known biologically active materials, including the salicylates, a class known for their activity as fluke control agents, and m-dialkylamino phenols which have features in common with a variety of known insecticides and herbicides.

Traditional methods for the synthesis of multiply-substituted anthranilic acid derivatives tend to be complicated and inefficient. By contrast, the present invention in another aspect provides a simple one-step process which results in high yield of a product.

This process depends essentially upon the self-condensation of an aminocrotonate by phosphorous oxychloride and the anthranilic acid derivatives so produced are of particular value as fungicides. Moreover, by simple chemical manipulations they can be readily converted into other derivatives of anthranilic acid, which also display anti-fungal properties.

In this aspect, the present invention provides a process for the production of a compound of formula I or formula II, which comprises the self-condensation of a compound of the formula III:

wherein R$^1$, R$^2$ and R$^7$ are as defined above, by reaction with phosphorous oxychloride, to form a compound of the formula II; followed, if desired, by replacement of substituents of the compound of the formula II in a manner known per se to form a compound of the formula I.

Reaction of the aminocrotonate of formula III in the presence of POCl$_3$ requires no special techniques. However, as the reaction is vigorously exothermic, care should be exercised in bringing the starting materials together, and it may be advisable to arrange for cooling of the reaction vessel. It has been found convenient to use an excess of POCl$_3$ as diluent, (preferably about five-fold, v/w), allowing the reaction to proceed smoothly and effectively. Preferably, the aminocrotonate of formula III is gradually added to such an excess of POCl$_3$ at a temperature of 25° C. or less, the mixture allowed to stand overnight at room temperature followed by isolation of the product ater removal of the major proportion of the POCl$_3$ in vacuo and hydrolysis of the remainder with icewater. In this way, yields of the product in excess of 70% may be obtained.

Typical compounds of the formula II which may be prepared according to the method of this invention are listed in Table 1.

Because of the activation of the substituted amino function in the compounds of the formula II, various electrophilic substitutions such as halogenation, formylation, thiocyanation, and nitration are easily performed in a manner known per se, thereby providing a useful synthetic route to compounds of the formula I. Examples of such compounds are set out in Table 2. Modification or removal of existing substituents on the compounds of the formula II to form other compounds of the formula I, is also possible, for example, by hydrogenolysis (dehalogenation) and hydrolysis, thus further enhancing the utility of these compounds as synthetic intermediates. Some such reactions are outlined below, and compounds so prepared are exemplified in Table 3.

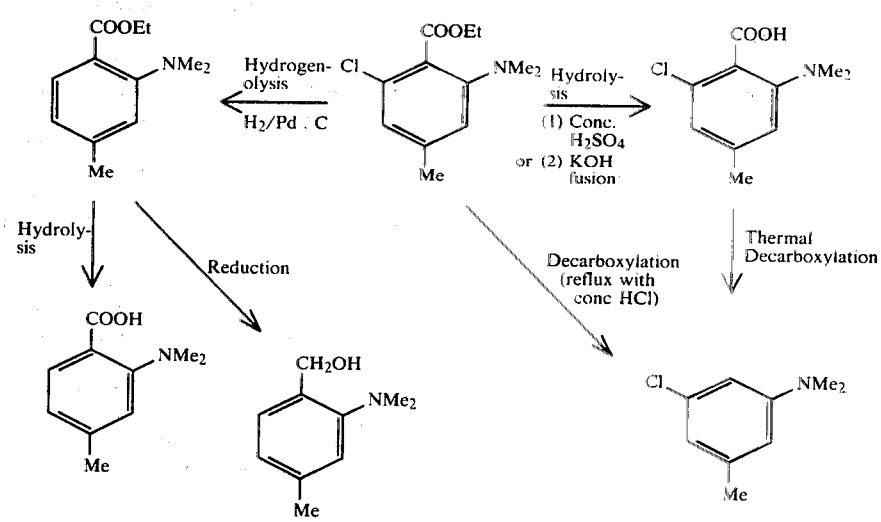

The invention will now be described in greater detail by reference to the following examples.

EXAMPLE I

Ethyl 6-chloro-4,N,N-trimethylanthranilate (Compound 1)

(Formula I, where $R^1=R^2=Me$, $R^3=Et$, $R^4=Cl$, $R^5=H$, $R^6=H$)

Ethyl β-dimethylaminocrotonate (100 g) was added slowly with stirring to $POCl_3$ (500 ml), cooled externally by a bath of tap-water. The addition was controlled so that the temperature did not exceed 35° C. The mixture was kept overnight, then heated on a steambath for 1 hour. Excess $POCl_3$ was removed in vacuo (rotary evaporator) and the residual brown oil treated with icewater (500 ml). After hydrolysis of residual $POCl_3$ was complete, the product was extracted with chloroform (3×150 ml), the combined extracts dried by filtration and the chloroform removed in vacuo. The residual oil (80 g) was distilled in vacuo to give ethyl 6-chloro-4,N,N-trimethylanthranilate as a pale yellow oil (60 g, 78%), $bp_{1.0}$ 124°–128° C.

EXAMPLE II

Ethyl 5-bromo-6-chloro-4,N,N-trimethylanthranilate (Compound 2)

(Formula I, where $R^1=R^2=Me$, $R^3=Et$, $R^4=Cl$, $R^5=Br$, $R^6=H$).

To a solution of ethyl 6-chloro-4,N,N-trimethylanthranilate (compound 1) (2.35 g) in acetic acid (10 ml), $Br_2$ (0.5 ml) was added dropwise with stirring. After 10 min, the pale pink solution was poured into water and the product extracted into chloroform (2×20 ml). The chloroform extracts were washed with water, then with saturated sodium carbonate solution, and after filtering dry, were evaporated to give compound 2 a colourless oil which was purified by distillation in vacuo $Bp_{0.8}$ 155°–160° C.

EXAMPLE III

Ethyl 3,5,6-trichloro-4,N,N-trimethylanthranilate (Compound 3)

(Formula I, where $R^1=R^2=Me$, $R^3=Et$, $R^4=R^5=R^6=Cl$)

Example II was repeated except that 1.7 ml $SO_2Cl_2$ was used instead of 0.5 ml $Br_2$, and the mixture was refluxed for 30 min. Work-up as before gave compound 3 as a pale yellow oil, $bp_{0.3}$ 126°–128° C.

EXAMPLE IV

Ethyl 6-chloro-4,N,N-trimethyl-5-thiocyanoanthranilate (Compound 4)

(Formula I, where $R^1=R^2=Me$, $R^3=Et$, $R^4=Cl$, $R^5=SCN$; $R^6=H$)

A suspension of lead thiocyanate (1.6 g) in acetic acid (20 ml) was stirred and sulphuryl chloride (0.8 ml) added. After 15–20 min, ethyl 6-chloro-4,N,N-trimethyl anthranilate (compound 1) (2.35 g) was added and the mixture stirred at room temperature for 3 hours. The precipitated lead chloride was removed by filtration and washed with acetic acid. The combined filtrates were poured into water and left overnight. The solid precipitate was collected and recrystallised from aqueous ethanol to give compound 4 as colourless needles, mp 96°–98° C.

The N,N-diethyl analogue (compound 5) (Formula I where $R^1=R^2=R^3=Et$, $R^4=Cl$ $R^5=SCN$ $R^6=H$) was prepared in a similar fashion and obtained as an oil.

EXAMPLE V

Ethyl-6-chloro-4,N,N-trimethyl-5-nitroanthranilate (Compound 6)

(Formula I, where $R^1=R^2=Me$, $R^3=Et$, $R^4=Cl$, $R^5=NO_2$, $R^6=H$)

Ethyl 6-chloro-4,N,N-trimethylanthranilate (compound 1) (3 g) was added dropwise with stirring to a solution of nitric acid (SG 1.43) (3 ml) in conc sulphuric acid (10 ml) at room temperature. The mixture was stirred overnight at room temperature, then poured into water (200 ml). The yellow product was extracted into chloroform, and the extracts were dried by filtration after washing with water. The solvent was removed and the residue crystallised from ethanol to give ethyl 6-chloro-4,N,N-trimethyl-5-nitroanthranilate (2 g) as yellow needles, mp 76° C.

The N,N-diethyl homologue (compound 7) (Formula I, where $R^1=R^2=R^3=Et$, $R^4=Cl$, $R^5=NO_2$, $R^6=H$)

was prepared by a similar procedure, as yellow needles mp 100° C.

EXAMPLE VI

Ethyl 6-chloro-5-formyl-4,N,N-trimethylanthranilate (Compound 8)

(Formula I, where $R^1=R^2=Me$, $R^3=Et$, $R^4=Cl$, $R^5=CHO$, $R^6=H$).

Ethyl 6-chloro-4,N,N-trimethylanthranilate (compound 1) (2.35 g) was added to a solution of POCl$_3$ (1 ml) in DMF (5 ml) and the mixture heated on a steambath for 8 hours. The mixture was poured into water, brought to pH 5 with sodium acetate and left for 3 hours. The product was extracted into chloroform (2×20 ml) and the washed, filtered extracts evaporated. Compound 8 was obtained as a pale yellow oil, which crystallized on standing, mp 63°–64° C.

The N,N-tetramethylene analogue (compound 9) (Formula I, where $R^1$, $R^2=-(CH_2)-$, $R^3=Et$, $R^4=Cl$, $R^5=CHO$, $R^6=H$) was similarly prepared as needles of mp 110° C.

EXAMPLE VII

Ethyl 4,N,N-trimethylanthranilate (compound 10)

(Formula I, where $R^1=R^2=Me$, $R^3=Et$, $R^4=R^5=R^6=H$)

Ethyl 6-chloro-4,N,N-trimethylanthranilate (compound 1) (7 g), 5% Pd/c catalyst (1 g), sodium acetate (7 g) and ethanol (100 ml) were shaken with hydrogen at 2 atmos. until uptake ceased. The mixture was filtered, evaporated to dryness and the residue shaken with water and chloroform. Evaporation of the chloroform gave compound 10 as a colourless oil.

EXAMPLE VIII

4, N,N-trimethylanthranilic acid (Compound 11)

(Formula I, where $R^1=R^2=Me$, $R^3=R^4=R^5=R^6=H$)

Ethyl-4,N,N,trimethylanthranilate (compound 10) (1 g) was heated under reflux with 10 ml 10% NaOH for 18 hours. The clear solution was acidified to pH 5 with acetic acid and extracted with chloroform. Evaporation of the filtered chloroform extract gave an oil which crystallised. Recrystallisation from chloroform-petroleum ether gave compound 11 was colourless prisms mp 166°–167° C.

EXAMPLE IX 2-dimethylamino-4-methylbenzylalcohol (Compound 12)

Ethyl 4,N,N-trimethylanthranilate (compound 10) (2 g) was added to a suspension of lithium aluminium hydride (0.4 g) in dry tetrahydrofuran (50 ml) and the mixture refluxed for 1 hour. Ethyl acetate was added to decompose excess hydride, and the mixture stirred with saturated ammonium chloride solution (10 ml) for 15 min, then filtered through celite. After addition of water to the filtrate, the organic layer was separated and the aqueous phase extracted with ether. The combined organic extracts were dried (MgSO$_4$) and evaporated to give the benzyl alcohol as a pale yellow oil, which could not be distilled in vacuo without decomposition.

EXAMPLE X 6-chloro-4,N,N-trimethylanthranilic acid (Compound 13)

(Formula I, where $R^1=R^2=Me$, $R^3=H$, $R^4=Cl$, $R^5=R^6=H$)

Ethyl 6-chloro-4,N,N-trimethylanthranilate (compound 1) (5 g) was cautiously added to conc sulphuric acid (10 ml) and the mixture heated on the steambath for 3 hours. The mixture was poured onto ice, made alkaline with NaOH and extracted with chloroform.to remove unreacted starting material. The alkaline phase was neutralised with acetic acid and extracted with chloroform. Evaporation of the filtered chloroform extract gave a colourless oil which crystallised. Recrystallisation from chloroform gave compound 13 as colourless prisms mp 119°–120° C. (decomp.).

EXAMPLE XI 5-chloro-N,N-dimethyl-m-toluidine (Compound 14)

6-chloro-4,N,N-trimethylanthranilic acid (Compound 13) (0.5 g) was heated in boiling o-xylene for 1 hour during which time CO$_2$ was evolved. The solvent was removed in vacuo and the residual oil purified by microdistillation to produce a colourless oil.

EXAMPLE XII

Ethyl 4-methyl-6-(1-morpholino) salicylate (Compound 15)

Ethyl-β-(1-morpholino)crotonate (18.5 g) was refluxed for 5 h with POCl$_3$ (10 ml) in benzene (100 ml). The reaction mixture was treated with water (200 ml) and stirred 30 min. The benzene layer was separated, washed with water, dried (MgSO$_4$) and evaporated leaving a brown oil (7.5 g). This oil was taken up in benzene (100 ml) and extracted with 10% HCl (4×25 ml). The acid extract was combined with the water layer obtained after decomposition of the reaction mixture and the combined acidic fraction neutralised (pH 7, ammonia) and extracted with chloroform (2×50 ml). This fraction was purified by passage through a column of silica gel and the pale yellow solid obtained after removal of chloroform was recrystallised from aqueous ethanol to give ethyl 4-methyl-6-(1-morpholino) salicylate as colourless needles, mp 53°–54°.

EXAMPLE XIII

3-Dimethylamino-5-methyl phenol (Compound 16)

Ethyl-6-chloro-4,N,N-trimethylanthranilate (2.4 g) and KOH (powdered, 1.5 g) were heated together in a test-tube with a free flame. After the initial reaction (temp 200°–220°) had subsided, the temperature was raised to 240°–260°, whereupon a second vigorous reaction ensued and the mixture became dark. On cooling, the mixture was dissolved in water, extracted with ether to remove tarry byproducts, and acidified (pH 5) with acetic acid. The crude product was extracted into chloroform and after removal of solvent, was purified by sublimation at 0.1 mm. 3-Dimethylamino-5-methylphenol was obtained as a pale yellow solid, mp 67°–68°.

EXAMPLE XIV

Fungicidal Activity

In vitro assays using compounds of the formula I were carried out as follows. An agar medium prepared from Difco "Bacto-Agar" and distilled water was sterilised in an autoclave. Aliquots of the test compounds in acetone solution were added to two duplicate samples of the medium to give final concentrations of 5, 10, 25, 50, 100 and 150 ppm, and the resulting solutions poured into sterilised petri dishes and inoculated with *Tilletia foetida* (wheat smut) from the kernels of infected wheat. The dishes were incubated at 10° C. in the dark for 8–9 days until controls (Agar without chemicals) shows 95–100% germination. The inhibition of germination due to the test compounds was then determined by estimating (microscope) the spores germinated as a percentage of control. The results are given in Table 4.

Table 1

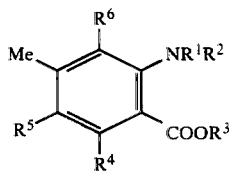

II

| $R^1$ | $R^2$ | $R^7$ | Yield % | Bp (Mp) °C. |
|---|---|---|---|---|
| Me | Me | Et | 78 | 124°–128°/1.0 mm |
| Et | Et | Et | 88 | 130°–132°/1.0 mm |
| —(CH$_2$)$_4$— | | Et | 89 | prisms mp 78°–79° (Ex MeOH) |
| C$_6$H$_{11}$ | H | Et | 33 | 150°–152°/0.2 mm |
| C$_3$H$_7$ | H | Et | 25 | 114°–116°/0.2 mm |

Table 2

| Compound No. | $R^1$ | $R^2$ | $R^3$ | $R^4$ | $R^5$ | $R^6$ | Yield % | Description |
|---|---|---|---|---|---|---|---|---|
| 2 | Me | Me | Et | Cl | Br | H | 75 | Colourless oil, bp 155°–160° C./0.8 mm |
| 3 | Me | Me | Et | Cl | Cl | Cl | 70 | Pale yellow oil, bp 126°–128° C./0.3 mm |
| 4 | Me | Me | Et | Cl | SCN | H | 73 | Colourless needles, mp 97°–98° C. |
| 6 | Me | Me | Et | Cl | NO$_2$ | H | 60 | Yellow needles mp 76° C. |
| 8 | Me | Me | Et | Cl | CHO | H | 77 | Colourless oil, bp 160°–165° C./0.8 mm |
| 7 | Et | Et | Et | Cl | NO$_2$ | H | 79 | Yellow needles mp 100° C. |
| 5 | Et | Et | Et | Cl | SCN | H | 83 | Colourless oil |
| 9 | —(CH$_2$)$_4$— | | Et | Cl | CHO | H | 75 | Colourless needles, mp 110° C. |

Table 3

| Compound No | Compound | Procedure | Yield % | Description |
|---|---|---|---|---|
| 10 | Ethyl-4,N,N-trimethylanthranilate | Hydrogenolysis | 95 | Oil |
| 11 | 4,N,N-trimethyl-anthranilic acid | Hydrolysis | 50 | Colourless needles mp 167°–168° C. |
| 12 | 2-dimethylamino-4-methyl benzylalcohol | Reduction | 84 | Oil, decomposing on distillation |
| 13 | 6-chloro-4,N,N-trimethylanthranilic acid | Hydrolysis | 45 | Prisms, mp 119°–120° C. |
| 14 | 5-chloro-N,N-dimethyl-m-toluidine | Decarboxylation | 93 | Oil |

Table 4

Activity of compounds of Formula I against *Tilletia Foetida*

| Compound | Minimum inhibitory concentration (ppm) which reduces germination to <20% control |
|---|---|
| $R^1 = R^2 = R^3 =$ Et | 25 |
| Compound 1 | 25 |
| Compound 3 | 5 |
| Compound 4 | <5 |
| Compound 6 | <5 |
| Compound 7 | 25 |
| Compound 5 | 10 |

We claim:

1. A process for the production of a compound of the formula II:

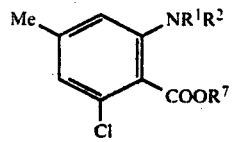

wherein $R^1$ and $R^2$ are the same or different and selected from the group consisting of a hydrogen atom and alkyl and cycloalkyl groups (provided that $R^1$ and $R^2$ are not both hydrogen atoms), or $R^1$ and $R^2$, together with the nitrogen atom to which they are attached, form a non-aromatic heterocyclic ring structure selected from the group consisting of a pyrrolidino, a piperidino and a morpholine group, and $R^7$ is an alkyl group, which comprises the self-condensation of a compound of the formula III

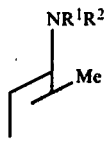

wherein $R^1$, $R^2$ and $R^7$ are as defined above, by reaction with phosphorous oxychloride, to form a compound of the formula II.

2. A process according to claim 1, wherein the self-condensation of the compound of the formula III is carried out in an excess of phosphorous oxychloride as diluent.

3. A process according to claim 2 wherein, upon completion of the reaction, the excess phosphorous oxychloride is removed in vacuo, and, if desired, the remainder hydrolysed with ice water.

4. A process according to any one of claims 1 to 3, wherein the self-condensation of the compound of the formula III is carried out at a temperature of 25° C. or less.

5. The process of claim 1 wherein $R^1$ and $R^2$ are the same or different and selected from the group consisting of a hydrogen atom an alkyl and cycloalkyl groups (provided that $R^1$ and $R^2$ are not both hydrogen atoms).

6. The process of claim 1 wherein $R^1$ and $R^2$, together with the nitrogen atom to which they are attached, form said non-aromatic heterocyclic ring structure.

* * * * *